United States Patent [19]

Ohata et al.

[11] 4,065,562

[45] Dec. 27, 1977

[54] METHOD AND COMPOSITION FOR REDUCING BLOOD GLUCOSE LEVELS

[75] Inventors: Katsuya Ohata, Uji; Hiroshi Enomoto, Kyoto; Yoshiaki Yoshikuni, Kyoto; Tatsuhiko Kono, Kyoto; Masahiro Yagi, Otsu, all of Japan

[73] Assignee: Nippon Shinyaku Co., Ltd., Japan

[21] Appl. No.: 752,006

[22] Filed: Dec. 20, 1976

[30] Foreign Application Priority Data

Dec. 29, 1975 Japan .............................. 50-157425
Jan. 1, 1976 Japan .................................... 51-239

[51] Int. Cl.$^2$ .......................................... A61K 31/445
[52] U.S. Cl. .................................................... 424/267
[58] Field of Search ........................................ 424/267

[56] References Cited

PUBLICATIONS

Chemical Abstracts, vol. 66, (1967), 85989q.

*Primary Examiner*—Frederick E. Waddell
*Attorney, Agent, or Firm*—Jacobs & Jacobs

[57] ABSTRACT

2-Hydroxymethyl-3,4,5-trihydroxypiperidine possesses antidiabetic and lipid biosynthesis inhibitory properties. The use of the compound for such indications and pharmaceutical compositions adapted to this use are described.

4 Claims, No Drawings

METHOD AND COMPOSITION FOR REDUCING BLOOD GLUCOSE LEVELS

DETAILED DESCRIPTION

This invention also relates to the use of the compound 2-hydroxymethyl-3,4,5-trihydroxypiperidine as medicament for humans and other animals. More particularly, this invention relates to the use of the compound as an antidiabetic agent and as an inhibitor of increased lipid biosynthesis.

If glucose is ingested, alone or in the form of carbohydrates such as maltose, sucrose, starch in food or drink, the blood glucose level rises abnormally. In the case of a healthy subject, such a hyperglycemic state is quickly normalized, the glucose in the blood being metabolized and utilized by the organism.

As a pre-diabetic condition advances into diabetes mellitus, however, the glucose tolerance of the patient is lowered and the abnormally high blood sugar levels are maintained for prolonged periods of time. It is obvious that such a condition is undesirable for the diabetic.

A similar reaction and response to that seen in man can also be observed in animals, including livestock, poultry, pet animals bred or kept animals such as those kept at a zoo, laboratory animals, fishes such as cultivated fishes or aquarium fishes, or insects such as silkworms which can develop symptoms of hyperglycemia.

The carbohydrates ingested into an organism appear in the blood in the form of glucose and are metabolized into lipids such as triglyceride, cholesterol, phospholipid and the like. Too large a carbohydrate intake results in increased biosynthesis of lipids, causing hyperlipemia and excessive accumulation of lipids, both in adipose tissue and in other systems in the organism, conditions which can lead to atherosclerosis, obesity, myocardial infarction and other kinds of heart diseases.

Hyperglycemia can also result in gastroenteric disorders. It has been already mentioned that hyperglycemia may result from excess intake of carbohydrates. Such high blood-sugar levels promote the secretion of insulin from the pancreas. If such condition continues or occurs repeatedly, the excess secretion of hydrochloric acid and pepsin, which can in some cases have a detrimental effect on the stomach and duodenum, can cause gastrisis, stomach ulcer or duodenal ulcer.

Diseases or disorders resulting from the hyperglycemia and increased lipid biosynthesis thus include diabetes, prediabetic disorders, hyperlipemia and heart troubles resulting therefrom, such as atherosclerosis, obesity or myocardial infarction, as well as gastroenteric disorders such as gastritis, gastric ulcer or duodenal ulcer.

The compound of the present invention has demonstrated the ability to inhibit or reduce the increase of glucose levels in humans and other animals which generally occurs upon administration of glucose or a glucose producing carbohydrate and further to inhibit lipid biosynthesis.

The compound, which is 2(R),3(R),4(R),5(S)-2-hydroxymethyl-3,4,5-trihydroxypiperidine, is known and can be obtained by described chemical methods. Alternatively, the compound can be extracted from the mulberry plant, as described in copending application Ser. No. 752,149, filed herewith Dec. 20, 1976.

The compound can be administered in a pharmaceutical composition or combined with food or drink.

The composition containing the compound can be prepared in the form of tablets, dragees, capsules, troches, globules, granules, powder, suppositories, injections, liquids, emulsions, suspensions, syrup, and the like, to be administered one or more times a day. It may also be administered in the form of a medicinal composition such as gel, paste, cream, chewing gum or any number of food products, particularly those high in carbohydrates.

The following are conventional components which can also be present in the pharmaceutical composition:

1. Fillers or extenders, such as starch, lactose, mannitol, etc.;
2. Binders, such as crystalline cellulose, methylcellulose and other cellulose derivatives, gum arabic, gelatin and polyethylene glycol, polyvinyl alcohol, polyvinyl pyrrolidone, etc.;
3. Wetting agents, such as glycerol;
4. Disintegrators, such as carboxymethyl cellulose (excluding sodium salts), crystalline cellulose, polyethylene glycol, etc.;
5. Solution retarding agents, such as carboxymethyl cellulose sodium salts and high molecular compounds thereof;
6. Absorption accelerator, such as tetraammonium compounds;
7. Surfactants, such as methyl alcohol, glycerol fatty acid esters, etc.;
8. Fluidizing agents, such as silicic acid anhydride, synthetic aluminum silicate, etc.;
9. Lubricants, such as talc, magnesium and calcium stearate, solid polyethylene glycol, etc.; and
10. Filming agents, such as AEA (registered trademark of Sankyo), MPM (registered trademark of Tanabe), shellac, TC-5 (registered trademark of Kyowa), etc.

The tablets, dragees, capsules, troches and globules prepared from the medicinal compositions of this invention may contain an ordinary coating agent or coating including an opacifying agent, and such coating material can include, for example, high molecular compounds or waxes.

The compositions can be prepared so that they will release the active principal for a long time in the digestive organs. Also, the compound can be microencapsulated, and then combined with one or more of the components listed in (1) to (10) above.

The medicinal compositions suited for preparing the suppositories include, for example, a water soluble base material such as polyethylene glycol, cacao butter, and other oil bases such as Witepsol (registered trademark of Dynamite Nobel AG). A surface active agent in such bases may also be present.

Auxiliaries used for preparing liquid compositions including injectable liquids, emulsions, suspensions and syrup include the following:

1. Solvents, such as water, ethyl alcohol, isopropyl alcohol, ethyl carbonate, benzyl alcohol, benzyl benzoate, propylene glycol, 1,3-butylene glycol, dimethyl formamide, fats, glycol, tetrahydrofurfuryl alcohol, and polyethylene glycol;
2. Surfactants, such as sorbitan fatty acid ester, polyoxyethylene sorbitan fatty acid ester, polyoxyethylene fatty acid ester, polyoxyethylene ether of hydrogenated castor oil, and lecithin;
3. Suspending agents, such as carboxymethyl sodium salts, cellulose derivatives such as methyl cellulose, tragacanth and gum arabic;
4. Preservatives, such as paraoxybenzoic acid ester, benzalkonium chloride, and sorbinates;

When these drugs are administered parenterally they should of course be sterilized and used in the form of an isotonic solution. Preferred examples of the isotonizing agent used for the purpose are common salt, glucose and sorbit, and if necessary a buffer may be added.

Any of the above-said solid or liquid medicinal compositions may contain a coloring matter, preservative, spicery, flavoring or sweetening agent.

As noted, the compound can be combined with foods such as bread and other pastries, soft drinks, candies and the like, or utilized in cosmetic preparations such as tooth pastes, gargles and the like.

For livestock, where the compound reduces the formation of fat and produces leaner meat, as well as combatting hyperglycemic conditions generally, the compound can be administered in veterinary compositions combined with the feed or drink. In the case of feed, the final concentration in the feed is 0.0001 to 10%, preferably 0.001 to 1% by weight.

The material is contained in an amount of about 0.1 to 99.5%, preferably 0.5 to 95%, in the medicinal compositions. Other medications such as an antidiabetic drug, antilipemic agent and the like may also be contained in addition to the compound of this invention.

As to the mode of administration, the oral route is most convenient. The compound can also be administered intramuscularly, intraabdominally, intravenously or rectally.

The daily dosage is generally 1 to 100 mg/kg, but such dosage may vary over this range depending on the intake of carbohydrates or the extent or conditions of the disease. In case of giving the medicament in great quantity, it is advisable to administer the daily dose in parts. It will be easily understood that it is most desirable to administer the medicament immediately after intake of carbohydrates.

The toxicity of the compound is very low, the $LD_{50}$ in the mice being over 1200 mg/kg in the case of oral administration and over 800 mg/kg in the case of intravenous administration.

The antidiabetic action of the compound of this invention can be conveniently observed in the following models.

Male Sprague Dawley rats of body weight of 150 to 200 grams are fasted overnight and glucose is then administered orally at the rate of 0.5 to 4 g/kg by using a stomach tube. Blood is drawn from the tail vein of each rat at suitable time intervals to determine glucose level in the blood. The glucose content in the blood increases rapidly to cause hyperglycemia. If the compound is administered simultaneously in an amount of 1 to 1000 mg/kg, rise of the glucose content in the blood is inhibited.

A similar effect of this material to humans is also attested by the following experiment.

When 50 to 100 grams of glucose and 1 to 1000 mg/kg of the compound are administered orally to healthy man and the glucose level in the blood is determined at suitable time intervals, as in the case of the rats, it is observed that rise of the glucose content in the blood is inhibited corresponding to the dosage of the material. A similar inhibitory action is also observed when starch or sucrose are administered in place of glucose in the foregoing experiment.

The following are some examples of this invention. These examples are merely a part of the experiments conducted for corroborating the fact that the compound of this invention has the blood sugar level controlling action to inhibit increase of glucose in the blood when carbohydrates are ingested, and hence the scope of this invention should not be thereby limited.

EXAMPLE 1

Inhibitory Action Against Increase of Glucose in Blood of Glucose-administered Rats Male Sprague Dawley rats with body weights ranging from 150 to 200 grams were fasted overnight, and then 2 g/kg of glucose was administered orally by using a stomach tube. The compound of this invention was also administered simultaneously in an amount of 10 to 100 mg/kg, and blood was drawn from the tail vein of each rat at suitable time intervals, and blood glucose levels were measured according to a method using glucose oxidase (Blood Sugar Test, TC-M-III, Boehringer Mannheim A.G.). The results are shown in Table 1 below.

Increase of glucose in the blood can be totally inhibited by administering the compound of this invention at the dose of 100 mg/kg.

Table 1

| Dose of the compound of this invention | Number of rats tested | Blood Glucose Concentration (mg%) Time (min) after administration | | | |
|---|---|---|---|---|---|
| | | 0 | 15 | 30 | 60 |
| Blank | 7 | 58 | 68 | 69 | 73 |
| 0 mg/kg | 6 | 55 | 110 | 140 | 145 |
| 10 | 5 | 59 | 100 | 108 | 107 |
| 100 | 5 | 52 | 59 | 58 | 63 |

Blank: Water alone was administered.

EXAMPLE 2

Inhibitory Action Against Increase of Blood Glucose for Sucrose-Administered Rats Male Sprague Dawley rats with body weight of 150 to 200 grams were fasted overnight, and 2 g/kg of sucrose was administered orally by using a stomach tube. The compound of this invention was simultaneously administered in a similar way at the rate of 1 to 100 mg/kg, and blood was drawn from the tail vein of each rat at suitable time intervals and blood glucose levels were measured by a method using glucose oxidase. The results are shown in Table 2 below.

Increase of glucose in the blood could be totally inhibited by administering the compound of this invention at the dose of 10 mg/kg.

Table 2

| Dose of the compound of this invention | Number of rats tested | Blood Glucose Concentration (mg%) Time (min) after administration | | | |
|---|---|---|---|---|---|
| | | 0 | 15 | 30 | 60 |
| (Blank) | 7 | 58 | 68 | 69 | 73 |
| 0 mg/kg | 6 | 61 | 107 | 133 | 135 |
| 1 | 5 | 69 | 98 | 121 | 127 |
| 10 | 6 | 47 | 57 | 52 | 97 |
| 100 | 5 | 52 | 66 | 63 | 64 |

Blank: Water alone was administered.

EXAMPLE 3

Inhibitory Action Against Increase of Blood Glucose for Starch-Administered Rats Male Sprague Dawley rats with body weight of 150 to 200 grams were fasted overnight, and 1 g/kg of starch was administered orally by using a stomach tube. The compound of this invention was simultaneously administered at the dose of 10 to 100 mg/kg, and blood was drawn from the tail vein of each rat and blood glucose levels were examined by a method using glucose oxidase. The results are shown in Table 3.

It was possible to totally inhibit increase of glucose in the blood by administering the compound of this invention at the dose of 100 mg/kg.

Table 3

| Dose of the compound of this invention | Number of rats tested | Blood Glucose Concentration (mg%) Time (min) after administration | | | |
|---|---|---|---|---|---|
| | | 0 | 15 | 30 | 60 |
| (Blank) | 7 | 58 | 68 | 69 | 73 |
| 0 mg/kg | 6 | 54 | 117 | 104 | 110 |
| 10 | 5 | 53 | 67 | 80 | 83 |
| 100 | 5 | 52 | 57 | 63 | 59 |

Blank: Water alone was administered.

What is claimed is:

1. The method of reducing blood glucose levels and inhibiting lipid biosynthesis in humans and other animals which comprises orally, rectally or parentally administering thereto an effective amount of 2-hydroxymethyl-3,4,5-trihydroxypiperidine.

2. A pharmaceutical composition for use in reducing blood glucose levels and inhibiting lipid biosynthesis which comprises an effective amount of 2-hydroxymethyl-3,4,5-trihydroxypiperidine and a nontoxic carrier.

3. The method of claim 1 wherein said 2-hydroxymethyl-3,4,5-trihydroxypiperidine is administered orally.

4. An animal feed comprising an amount of 2-hydroxymethyl-3,4,5-trihydroxypiperidine effective to inhibit lipid biosynthesis in combination with an edible carrier.

* * * * *